Figure 1:
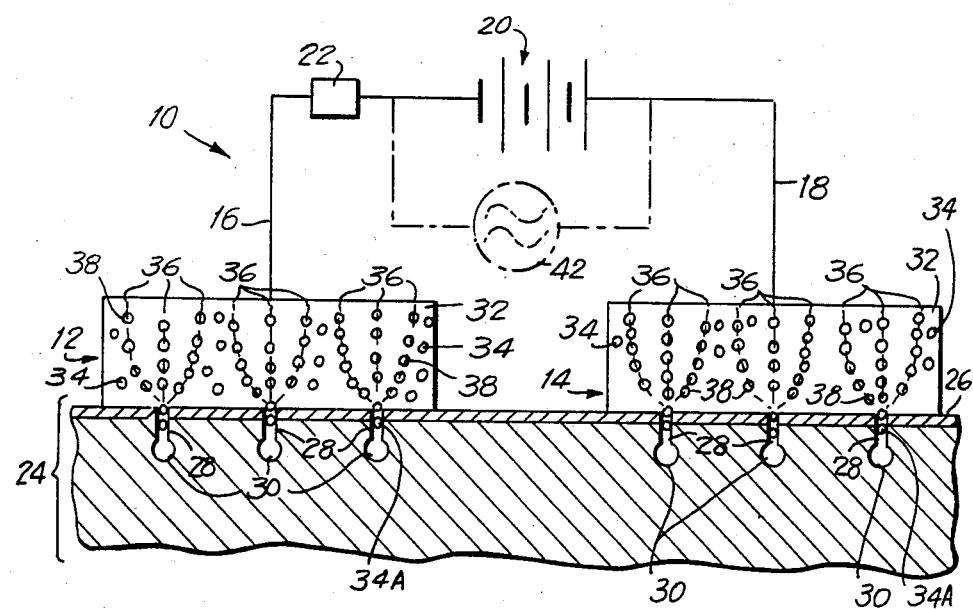
Figure 1A:
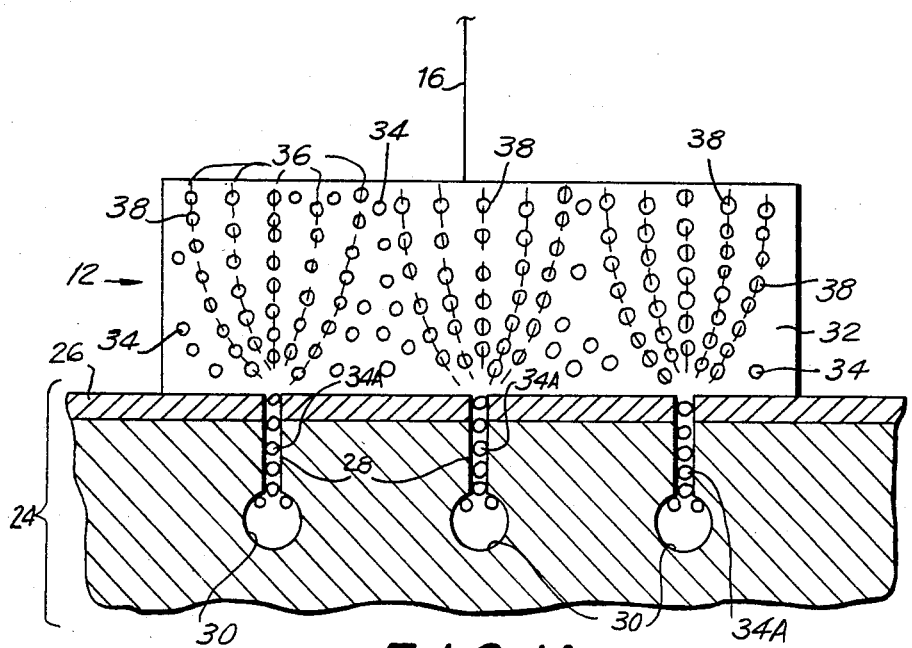

United States Patent [19]

Sibalis

[11] Patent Number: 4,734,090
[45] Date of Patent: Mar. 29, 1988

[54] ELECTRICAL TRANSDERMAL DRUG APPLICATOR

[75] Inventor: Dan Sibalis, Stony Brook, N.Y.

[73] Assignee: Drug Delivery Systems Inc., New York, N.Y.

[21] Appl. No.: 888,151

[22] Filed: Jul. 18, 1986

[51] Int. Cl.⁴ ............................................. A61N 1/30
[52] U.S. Cl. ..................................... 604/20; 128/783; 128/798
[58] Field of Search ............... 128/783, 798, 799, 803; 604/20, 21

[56] References Cited

U.S. PATENT DOCUMENTS 4,142,521  3/1979  Konikoff ........................... 128/82.1
4,416,274  11/1983  Jacobsen et al. .................... 128/803

*Primary Examiner*—Lee S. Cohen
*Assistant Examiner*—Randy Citrin
*Attorney, Agent, or Firm*—Lackenbach Siegel Marzullo & Aronson

[57] ABSTRACT

A transdermal drug applicator for passing at least one drug for delivery to the systemic circulation system of a patient through the skin. The applicator includes a drug applicator containing a colloidal suspension having at least one drug for delivery to the body of a patient, the colloidal suspension comprising a fluid medium and generally large, as compared to the size of molecules, particles in the fluid medium. The particles and the medium are of different permittivities. The drug reservoir is capable of being placed in electrical contact with the skin of the patient. A voltage device imposes electrostatic field lines upon the fluid medium so as to create a non-uniform electrostatic field in the fluid medium when the drug reservoir is placed on the skin. The particles migrate in accordance with the principle of dielectrophoresis so as to pass through the skin into the systemic circulation system.

29 Claims, 10 Drawing Figures

ELECTRICAL TRANSDERMAL DRUG APPLICATOR

RELATED U.S. PATENT APPLICATIONS

This application is also related to my U.S. Pat. No. 4,557,723 and to my pending U.S. patent application Ser. No. 660,192, U.S. Pat. No. 4,662,031. This application is also related to copending U.S. patent application Ser. No. 839,050, U.S. Pat. No. 4,640,689; PCT/US85/01074 and PCT/US85/01075 both filed June 10, 1985; U.S. patent application Ser. No. 807,234; and U.S. patent Ser. No. 778,183.

FIELD OF THE INVENTION

This invention relates to transdermal delivery of a drug, and more specifically relates to transdermal delivery of a drug using principles of dielectrophoresis alone or in combination with other electrokinetic phenomena.

BACKGROUND OF THE INVENTION

Reference to or disclosure of devices for transdermal delivery of drugs by application of electrical current through the skin of a person or animal are shown in the following United States patents:

| | |
|---|---|
| 385,556 | 4,243,052 |
| 486,902 | 4.325.367 |
| 588,479 | 4,367,745 |
| 2,493,155 | 4,419,019 |
| 2,267,162 | 4.474.570 |
| 2,784,715 | 4.406,658 |
| 3,163,166 | 4.314,554 |
| 3,289,671 | 4,166,457 |
| 3,547,107 | 4,239,052 |
| 3,677,268 | 4,290,878 |
| 4,008,721 | 4,164,226 |
| 4,141,359 | 4,362,645 |
| 4,239,046 | 4,273,135 |

The following foreign patents refer to or disclose transdermal delivery devices:
EPA No. 0060452
DE No. 290202183
DE No. 3225748
EPA No. 0058920
UK No. 2104388

DISCUSSION OF THE PRIOR ART

In the prior art, the systems for delivery of a medicament through the skin have been based upon the principles of electrophoresis and/or electro-osmosis where drug molecules in solution are made subject to an electrostatic field created by an electric current. In electrophoresis, if the electrode having the same charge as that of the ionized drug molecules is above the solution, or reservoir, adjacent to the skin into which the ionized molecules are being transferred, then the ions will be repelled from that electrode and be instead directed to the skin through which the ionized molecules migrate into the blood stream. In electro-osmosis the solution is waterbased, which is usually attracted to the negative electrode; an electric current that passes through the porous membrane of the reservoir and the skin causes a flow of solution therethrough.

In the prior art, certain problems can occur by way of the fact that current being applied to the reservoir will naturally tend to bypass the stratum corneum (the horny layer), which acts as a natural electrical insulator, and concentrate at the ducts of the sweat glands. The passage of concentrated current at the sweat ducts can cause uncomfortable tingling and overheating at the ducts. In addition, concentration of current at the sweat ducts causes loss of potential useful delivery surface at the stratum corneum, which is far greater in area than the sweat ducts. It is noted that electrokinetic drug delivery is accomplished through the stratum corneum, but this delivery is difficult to accomplish due to the existence of electrical shunts, namely, the sweat ducts. In addition, the stratum corneum is a natural barrier against the diffusion of most medication.

The principle of dielectrophoresis differs from electrophoresis and electro-osmosis in several ways. One reference that sets forth the principle is *Dielectric and Electronic Properties of Biological Materials* by Ronald Pethig, John Wiley & Sons, 1979, in particular Chapter 6, pp. 186–206. This reference is incorporated into this application by reference. A copy of pages 186–206 are attached hereto and expressly made a part of this disclosure.

A brief discussion of the principle of dielectrophoresis is as follows. A particle possessing a net positive charge placed in a uniform electrostatic field will experience a force and will be pulled along the electrostatic field lines towards the electrode of opposite polarity. A charged particle placed in a non-uniform electrostatic field will behave in essentially the same manner and will be attracted towards the electrode of opposite polarity to its own net charge.

The behavior of a neutral particle is different. In a uniform electrostatic field the neutral particle will merely become polarized, with a positive charge being induced on the side nearest the cathode and the negative charge on the opposite side nearest the anode. Since the particle is electrically neutral, then these two regions of induced charge will be of equal magnitude. No net force will act upon this neutral particle in a uniform electrostatic field, and it will remain motionless unless subjected to forces arising from other effects.

In a non-uniform electrostatic field, however, the behavior of a neutral particle is different. The neutral particle will again become polarized, but now a net force will act upon the particle so as to give it a translational motion towards the region of strongest electrostatic field. This motion occurs where the electrostatic field to one side of the neutral particle is greater than the electrostatic field to the other side. (The electrostatic field intensity is proportional to the number of electrostatic field lines per unit area.) The induced positive and negative charge on the sides of the particle will still have equal magnitudes, so that the net force pulling the particle towards the cathode to the left will exceed that pulling it towards the low electrostatic field direction of the anode to the other side. This net force producing the translational motion is termed the dielectrophoretic force. It is to be particularly noted that if the polarity of the electrode arrangement were to be reversed, the neutral particle would still move towards the one side, in other words towards the region of greatest intensity.

It is also noted that in an alternating electrostatic field, charged particles will always tend to move towards the electrode having the opposite polarity to its own net charge. A neutral particle, on the other hand, will tend towards the electrostatic field region of maximum intensity, no matter what is happening to the polarity of the electrode producing the region of maximum electrostatic field intensity.

Dielectrophoresis has been defined as the motion of matter caused by polarization effects in a non-uniform electrostatic field, where the most polar matter moves towards the region of greatest electrostatic field intensity.

Dielectrophoresis is concerned with the motion of electrically uncharged particles. It requires strong divergent electrostatic fields, large particles, and high electrostatic field strengths. When the electric permittivity (a measure of dielectric; of how easy electrostatic lines go through an electrostatic field) of the surrounding fluid is greater than the permittivity of a particle in an electrostatic field, the particle will move to the area of a concentrated, strong electrostatic field. If the particle is anisotropic or non-symmetric in shape, the electrostatic field will align it along the electrostatic field direction. If the permittivity of the surrounding electrostatic field exceeds that of the particle, the particle is directed towards the weakest electrostatic field intensity.

SUMMARY OF THE INVENTION

The basis of the present invention is to create a reservoir that is a colloidal suspension of two materials that have different permittivities. The reservoir must first be treated so that a non-uniform electrostatic field is created when the reservoir containing the transdermal drug is placed against the skin.

The creation of a non-uniform reservoir is capable of occurring in that the sweat ducts themselves will create a non-uniform electrostatic field in the reservoir when the reservoir is placed against the skin. Because the skin includes a neutral barrier or insulation surface, the stratum corneum, the ionic current flow takes place mainly through the sweat ducts, thus causing a concentration of electrostatic lines at the sweat ducts.

The features of the present invention use the principle of dielectrophoresis to deliver the transdermal drug or drugs. One embodiment of the invention directs drug particles in a colloidal suspension directly to the sweat ducts where the drug particles are directly absorbed into the body. This process involves an electrical current significantly below that required by the prior art. Another embodiment of the invention involves as a first step of the inventive system to have oil particles in the colloidal suspension making up the reservoir clog up the ducts of the perspiration glands so as to shut off that ionic shunt pathway. As a second step of the system, delivery of the drug then takes place by migration of the drug in accordance with electro-osmosis or electrophoresis through substantially the entire stratum corneum, which, because of the passage of electrical current through it, changes from a layer of low permeability to one of high permeability. The particles to be delivered dielectrophoretically are relatively large as compared to molecule size. Particles could contain medication to cause active contraction and shutdown of the ducts of the perspiration glands.

In the present invention the composition of the colloidal drug reservoir determines the electro-biological basis in accordance with which delivery of the drug occurs. The drug reservoirs contain a colloidal suspension having at least one drug and comprising a fluid medium and generally large particles as compared to the size of molecules in the fluid medium. The drug may be in either the fluid medium or the large particles. The medium and the particles are of different permittivities. The reservoir is adapted to be placed in electrical contact with the skin of the patient.

In a first aspect of the invention, the colloidal suspension is water-based drug particles in an oily fluid medium. In a second aspect of the invention, the colloidal suspension is oil-based drug particles in an water medium. In a third aspect of the invention, the colloidal suspension is oil-based particles in a water-based drug fluid medium.

It is noted that the invention causes charged particles as well as neutral particles to be directed along the electrostatic field lines.

In the first case, the neutral water-based drugs are directed to the sweat ducts in accordance with the principle of dielectrophoresis in the non-uniform electrostatic field by the electrostatic field lines. Drug delivery takes place within the sweat ducts and glands in accordance with the principles of osmosis, electro-osmosis, and/or electrophoresis. This colloidal mixture has the advantage that the oily fluid medium prevents contamination of the drug. In addition, the water-based drug can be delivered with a small amount of current; a high electrostatic field strength is needed. This result avoids one of the problems of the prior art.

In the second case, the oil-based drug particles are moved along the electrostatic field lines in accordance with the principle of dielectrophoresis in the non-uniform electrostatic field to the sweat ducts and glands from where the drug diffuses into the circulatory system. This process proceeds in accordance with various electrokinetic phenomena, including electro-osmosis and electrophoresis. When the oil-based drug particles build up in the sweat ducts faster than they are absorbed by the body, they eventually clog the sweat ducts so as to cause an increase of resistivity of the sweat ducts to approximately the same value as the resistivity of the stratum corneum. At this time the electrostatic field lines are directed away from the sweat ducts to the surface of the stratum corneum so as to create a quasi-uniform electrostatic field, which action causes the oil-based drug particles to be moved to the general surface of the stratum corneum from where the drug particles are delivered through the electrically permeability-enhanced stratum corneum to the body. When the drugs in the sweat ducts are absorbed thus reducing the electrical resistance of the sweat ducts, an automatic feedback process is established wherein fresh delivery of the oil-based drug particles into the sweat ducts will proceed along with absorption into the body therefrom until the electrical resistance at the sweat ducts increases again to approximately the same value as the electrical resistance of the stratum corneum, so that the drug is delivered yet again to the stratum corneum. Damage to the sweat ducts due to excess current density is thus avoided while at the same time a constant and efficient delivery of the drug to the body proceeds.

In the third case, inert oil-based particles are directed along the electrostatic lines of force in the non-uniform electrostatic field to the sweat ducts so as to clog the ducts. At this point the medium is changed from a non-uniform electrostatic field state to a quasi-uniform electrostatic field state wherein the water-soluble drug migrates and/or is delivered through the entire stratum corneum in accordance with electrophoresis and electro-osmosis aided by the enhancement of skin permeability by the substantially even distribution of electrical current. It is noted that in this reservoir composition, current passes through the entire water-based reservoir from the beginning. This fact causes subtle differences in the occurrences of the phenomena from the first case previously described. These differences are not discussed in detail here as they are not directly related to the invention.

In all the above cases, it is desirable and beneficial that the permittivity of the fluid medium be similar to the permittivity of the skin hairs so as to minimize the amount of particles deposited on the hairs.

It is to be particularly noted that the passage of even a small amount of electrical current through the stratum corneum causes a multi-fold increase in the permeability of the stratum corneum so that even large drug molecules are able to pass the stratum corneum into the body with relative ease. The prior art is unable to use such a phenomenon efficiently since the sweat ducts still have much greater electrical conductivity than the stratum corneum despite its great increase of permeability with the result that most of the current still follows the ducts and the drug is not efficiently passed via the stratum corneum.

The present invention avoids many of the problems associated with previous devices for transdermal delivery of drugs, particularly problems associated with excessive current at the sweat ducts.

It is thus a principal object of the present invention to provide a system for transdermal delivery of a drug by providing a colloidal suspension containing at least one drug and comprising large particles and a fluid medium capable of being made into a non-uniform electrostatic field and directing the particles along electrostatic field lines imposed by voltage means in accordance with the principle of dielectrophoresis to the sweat ducts so that the drugs migrate or are delivered to the body from either the sweat ducts or from the stratum corneum, which has been permeability enhanced by the passage of electricity.

It is another object of the present invention to provide a system for transdermal delivery of a drug by providing a colloidal suspension containing at least one drug and comprising large particles in a fluid medium capable of being made into a non-uniform electrostatic field by voltage means and directing oil particles to the sweat ducts in accordance with the principle of dielectrophoresis so as to clog the sweat ducts and so create a generally uniform electrostatic field to enhance the permeability of the stratum corneum so that the drug or drugs pass efficiently through the stratum corneum into the body.

BRIEF DESCRIPTION OF THE DRAWINGS

FIG. 1 is a schematic view of a drug applicator system having a battery-driven electrical circuit having two colloidal suspension drug reservoirs comprising water-based drug droplets in an oily fluid medium with the mediums of the reservoirs in a non-uniform state;

FIG. 1A is a schematic view of the drug reservoir shown in FIG. 1 in isolation with electrostatic lines of force imposed on the colloidal suspension leading to the sweat ducts so as to create a non-uniform electrostatic field;

FIG. 2 is a schematic view of a drug applicator system having an electret that creates a non-uniform electrostatic field in a single reservoir, which contains a colloidal suspension comprising water-based drug particles in an oily fluid medium;

FIG. 3 is a schematic view of a drug applicator system having both a battery-driven reservoir comprising non-colloidal materials and an electret-charged, non-uniform electrostatic field reservoir containing a colloidal suspension comprising water-based drug particles in an oily fluid medium;

FIG. 4 is a schematic view of a drug applicator system having a battery-driven electrical circuit having a drug reservoir containing a colloidal suspension comprising oil-based drug particles in a water medium with the medium in a non-uniform state;

FIG. 4A is a detail view of the drug reservoir shown in FIG. 4 with the medium in a quasi uniform state;

FIG. 4B is a detail view of the drug reservoir shown in FIGS. 4A and 4B with the medium shown in a non-uniform state;

FIG. 5 is a schematic view of a drug applicator system having a battery-driven electrical circuit with two reservoirs containing colloidal suspensions comprising oil-based particles in a water-based medium with the mediums in non-uniform states;

FIG. 5A is a detail view of one of the reservoirs shown in FIG. 5 with the medium in a uniform state; and FIG. 6 is a schematic view of a drug applicator having both a battery-driven resevoir having a colloidal suspension comprising water-based drug droplets in an oily fluid medium in a non-uniform state and an electret charged, non-uniform electrostatic field reservoir containing a colloidal suspension comprising water-based drug particles in an oily fluid medium.

DESCRIPTION OF THE PREFERRED EMBODIMENTS

Reference is now made in detail to the drawings, wherein the numerals refer to the same or similar elements throughout.

A drug applicator system 10 shown in FIG. 1 includes a plurality of drug reservoirs, for example, two drug reservoirs 12 and 14 connected by conductors 16 and 18, respectively, to the negative and positive terminals, respectively, of a battery 20. A current conditioner 22 is connected in series on one of the terminal sides of battery 20 along conductor 18. Reservoirs 12 and 14 are shown lying in close contact with the skin 24 of a patient, and in particular in close contact with the stratum corneum 26 so that electrical current is capable of passing between the reservoirs, which act as electrodes, and the skin. FIG. 1A shows reservoir 12 in isolation. A plurality of sweat pores lead to sweat ducts 28, shown as three in the drawing for purposes of exposition, which lead to sweat glands 30 embedded in skin 24. The pores of ducts 28 open at the undersurfaces of reservoirs 12 and 14.

Reservoirs 12 and 14 are shown in this example to have the same colloidal suspension which includes an oily fluid medium 32 and water-based drug droplets, or particles, 34. Particles 34 are fairly large in size as compared to the size of a molecule. The permittivity of medium 32 and drug particles 34 are different. An electric circuit exists between battery 20, reservoir 12, skin 24, reservoir 14, and battery 20. Battery 20 generates sufficient voltage to impose electrostatic field lines 36 upon mediums 32 of both reservoirs 12 and 14. Electrostatic field lines 36 are formed in groups according to sweat ducts 28 so that each group of electrostatic field lines 36 converges at each duct 28 and widens to generally equal areas as they move toward at the topside of each reservoir 12 and 14. This formation of electrostatic field lines 36 is caused by the path of least electrical resistance created by ducts 28 at stratum corneum 26, which acts as an electrical insulator besides having a low permeability to the passage of fluids. The convergence of electrostatic field lines 36 at ducts 28 creates a electrostatic field intensity that is greater at ducts 28 than towards the topside of reservoirs 12 and 14 so that a non-uniform electrostatic field is created in the proximity of sweat ducts 28. The non-uniform electrostatic field contains primarily neutral, polarized drug particles 34, but charged particles 34 are not excluded from existence in the electrostatic field. Oily medium 32, being naturally resistant to current flow as compared to other fluids, such as water, conducts little electrical current. Neutral, polarized, water-based drug particles 34 align themselves in "pearl" chains along electrostatic field lines 36 and follow these lines into ducts 28 so as to enter the ducts as indicated as drug particles 34A in FIGS. 1 and 2. At this time water-based drug particles 34A migrate from sweat ducts 28 and from sweat glands 30 into the body.

It is noted that the polarity of the battery 20 is not relevant for the imposition of electrostatic field lines 36 since the principle of dielectrophoresis is independent of polarity. Once drug particles 34A are in ducts 28, however, the principle by which the drug particles enter the body is dependent upon the polarity of battery 20. That is, when the charge at the terminal of battery 20 that is connected to conductor 16 leading to reservoir 12 is positive, then the principle of migration of drug particles 34A in sweat ducts 28 at reservoir 12 is electrophoresis and the principle of migration of the drug particles at reservoir 14 is electro-osmosis. When the polarity of battery 20 is reversed, the principle of migration of the drug from the reservoirs is likewise reversed.

Applicator system 10 preferably use a DC/DC or AC/DC converter 42 in lieu of battery 20 so as to convert a low voltage battery to a high voltage for the purpose of imposing electrostatic field lines 36 in oily mediums 32 of reservoirs 12 and 14. Such a converter increases voltage since voltage is the factor in the primary phase of operation, namely, imposition of electrostatic field lines 36 in mediums 32 in reservoirs 12 and 14, and is independent of polarity. Current, however, does play a role in the delivery of drug particles 34 in accordance with the principle of electrophoresis and electro-osmosis.

Dielectrophoresis operates independently of the polarity of the power source since the requirement of a non-uniform electrostatic field is met by the formation of electrostatic field lines converging at sweat ducts 28.

Figure 2:
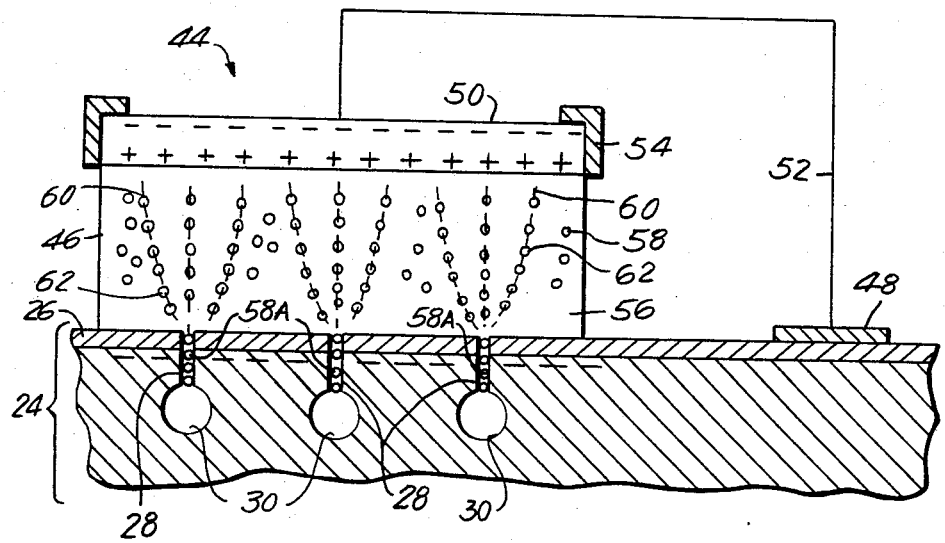

Another embodiment of the invention is shown as a drug applicator system 44 in FIG. 2, which includes a drug reservoir 46 and an optional skin electrode 48 connected to a permanently polarized electret 50 by a conductor 52. Electret 50 is oriented with its positive side in contact with reservoir 46 and its negative side in contact with shunt line 52. The system would operate equally if the charges shown were reversed. Electret 50 is isolated from any loss of charge by insulation 54. Reservoir 46 contains a colloidal suspension that includes an oily fluid medium 56 and large water-based drug particles 58; medium 56 and drug particles 58 have different permittivities. Upon the application of reservoir 46 and optional electrode 48 against stratum corneum 26 by a user, electrostatic field lines 60 are imposed upon oily medium 56 that converge at sweat ducts 28 at the surface of stratum corneum 26. Electret 50 imposes a negative field at its contact with reservoir 46 and a negative field is created at the stratum corneum. Upon the imposition of electrostatic field lines 60, which converge at sweat ducts 28 so as to create a non-uniform electrostatic field in medium 56, electrically neutral, polarized, water-based drug particles 58 align themselves along pearl chains 62, which converge in groups at each sweat duct 28. Drug particles 58 then proceed to enter sweat ducts 28 in accordance with the principle of dielectrophoresis; the drug particles are indicated as 58A in the ducts. Migration of drug particles 58 from ducts 28 into the body proceeds primarily according to the principle of electro-osmosis.

Electrostatic field conductor 52 provides a path for electrostatic field lines that would otherwise form a closed loop in the air, which has low permittivity, with the undesirable result that electrostatic field lines would be distorted in oily medium 56. Skin electrode 48 can optionally be insulated from the skin so that current cannot pass and only electrostatic field lines can pass.

Electret 50 is capable of imposing a high voltage on medium 56 since the oily medium is resistive to the formation of electrostatic field lines.

Figure 3:
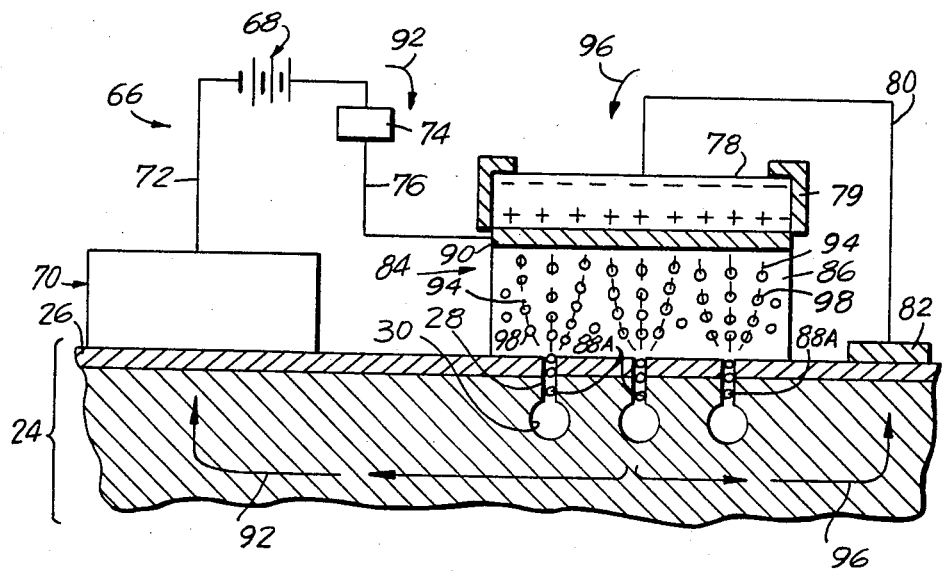

Another embodiment of the invention is shown as drug applicator system 66 in FIG. 3, which includes a battery 68 connected to a drug reservoir 70 by a conductor 72 connected to the negative terminal of battery 68. A current conditioner 74 is positioned is series with battery 68 via conductor 76. Reservoir 70 is of the type described in my previous patents and patent applications, and the drug to be delivered is in solution as a liquid or a gel in the reservoir. Applicator system 66 also includes a permanently polarized electret 78 connected on its negative side to an electrostatic field conductor 80 that in turn is connected to a skin electrode 82 in electrical contact with skin 24, and in particular stratum corneum 26, of the patient. Electret 78 is protected from voltage loss by insulator 79. Another drug reservoir 84 containing a colloidal suspension of the type previously described relative to applicator system 10 including an oily fluid medium 86 and large waterbased drug particles 88 having a different permittivity from medium 86 is in electrical connection to both electret 78 and conductor 76 at a common electrode 90 that is positioned between electret 78 and reservoir 84.

When reservoirs 70 and 84 are placed in contact with the skin of the patient, in particular stratum corneum 26, an electrical battery-driven circuit 92 is created between battery 68, common electrode 90 via conductor 76, reservoir 84, skin 24, reservoir 70, and battery 68 via conductor 72. This electrical current causes migration of the drug in reservoir 70 through stratum corneum 26 into the skin of the patient in accordance with electro-osmosis.

At the same time electrostatic field lines 94 that converge at sweat ducts 28 are imposed upon medium 86 of reservoir 84 so as to create a non-uniform electrostatic field in medium 86. An electret-driven electrostatic circuit 96 is created between electret 78 and reservoir 84 via common electrode 90, skin 24, and the negative side of electret 90 via conductor 80. Neutral, polarized, water-based drug particles 88 form pearl chains 98 along electrostatic field lines 94 so that drug particles 88 migrate in accordance with the principle of dielectrophoresis along electrostatic field lines 94 into sweat ducts 28, the particles there being shown as drug particles 88A. Electrical current 92 established by battery 68 also enhances and controls the delivery of drug particles 88 through skin 24.

It is noted that in each of the embodiments of the invention set forth above, namely, drug applicator systems 10, 44, and 66, have had at least one reservoir containing a colloidal suspension that comprises an oily fluid medium with relatively large, water-based drug particles suspended in the fluid medium. One advantage of this particular colloidal suspension is the that oily fluid medium has a high electrical resistance, which avoids damaging the sweat ducts with an excessive current.

Figure 4:
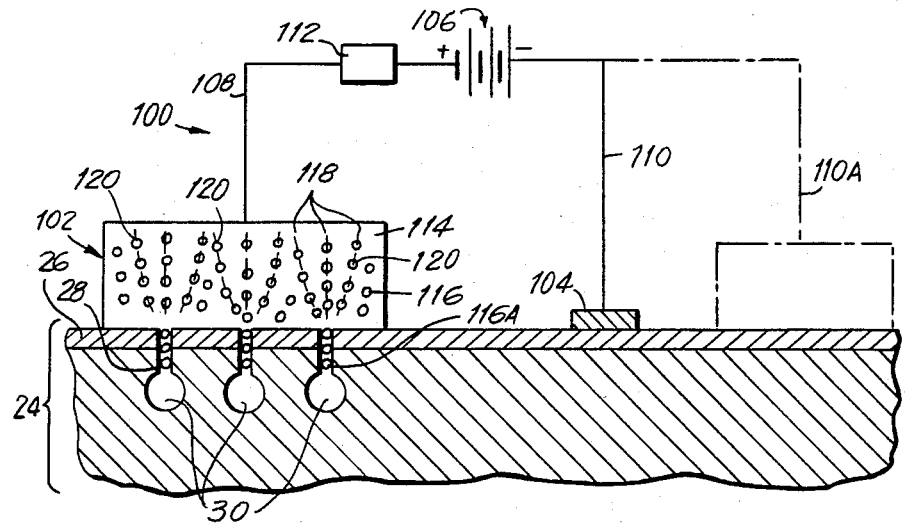
Figure 4A:
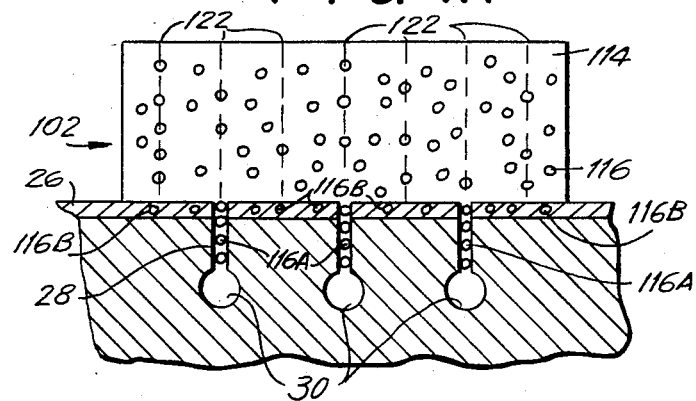
Figure 4B:
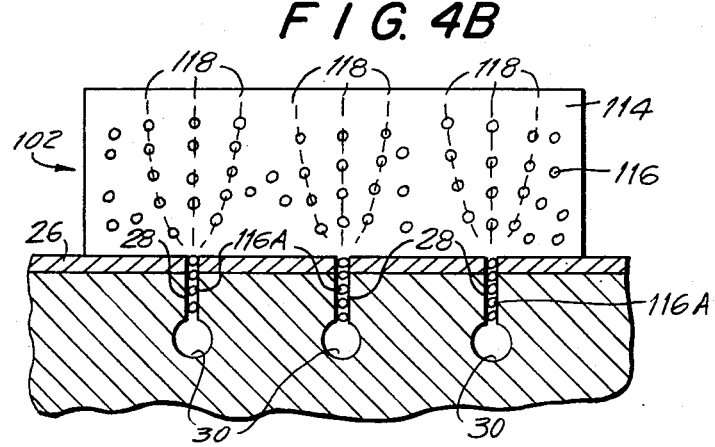

Another embodiment of the invention that accomplishes the same result is a drug applicator system 100 shown in FIGS. 4, 4A, and 4B. Applicator system 100 includes a drug reservoir 102 and a skin electrode 104 connected in series with a battery 106 by positive-side and negative-side conductors 108 and 110, respectively. A current conditioner 112 is connected in series with battery 106 via conductor 108. Reservoir 102 contains a colloidal suspension that includes a water medium 114 and relatively large oil-based drug particles 116 having a different permittivity from medium 114. When reservoir 102, which acts as an electrode, and skin electrode 104 are placed upon skin 24, particularly at stratum corneum 26, an electric circuit is created between reservoir 102, skin 24, and battery 106. At this time, electrostatic field lines 118 are created in water medium 114 along which pearl chains 120 comprising neutral, polarized drug particles 116 are formed leading to sweat ducts 28 at the surface of stratum corneum 26. Movement of neutral (and charged) oil-based drug particles 116 are moved along pearl chains 120 in accordance with the principle of dielectrophoresis into sweat ducts 28 and even as far as sweat glands 30, where the drug particles are indicated by numeral 116A. Drug particles 116A diffuse into the circulatory system of the patient in accordance with various electrokinetic phenomena, including electro-osmosis and electrophoresis. Oil-based drug particles 116A eventually build up faster in sweat ducts 28 than they are absorbed into the circulatory system. This results an increase in the value of the electrical resistivity of sweat duct 28 to approximately the same value as the electrical resistivity of stratum corneum 26. At this time a quasi-uniform electrostatic field is created so that new electrostatic field lines 122 are directed away from sweat ducts 28 throughout the volume of reservoir 102 over the general surface of stratum corneum 30, as shown schematically in FIG. 4A. Current then is directed along the new electrostatic field lines 122, shown schematically, through the entire stratum corneum 26. The passage of current through generally the entire surface of stratum corneum 26 greatly enhances the permeability of the stratum corneum to the migration of the entire colloidal system including oil-based drug particles 116. The drug particles, indicated as drug particles 116B in FIG. 4A, are delivered through the electrically permeability-enhanced stratum corneum 26 into the systemic circulation system of the body in accordance with the principles described in my previous patents and patent applications mentioned above. When drug particles 116A in sweat ducts 28 are absorbed into the body so as to reduce the electrical resistance of sweat ducts 28 sufficiently to reestablish electrostatic field lines 118 at sweat ducts 28 so as to create once again a non-uniform electrostatic field, fresh delivery of drug particles 116A to the sweat ducts and glands along with absorption therefrom will proceed once again, as is shown in FIG. 4B. This feedback phenomena of alternating delivery of drug particles 116 between the stratum corneum and the sweat ducts continues throughout the process of delivery of the drug from the reservoir until the drug is depleted from the reservoir.

An optional drug reservoir 124 shown in phantom line in FIG. 4 can be substituted for electrode 104 by a conductor 110A, which is in lieu of connector 110.

Water medium 114 conducts electricity, which is a different result from that described in oily mediums 32, 56, and 86 of applicator systems 10, 44, and 66.

It is noted that applicator system 100, like systems 10, 44, and 66, reduces the current level at sweat ducts 28 in accordance with the principle of dielectrophoresis.

Figure 5:
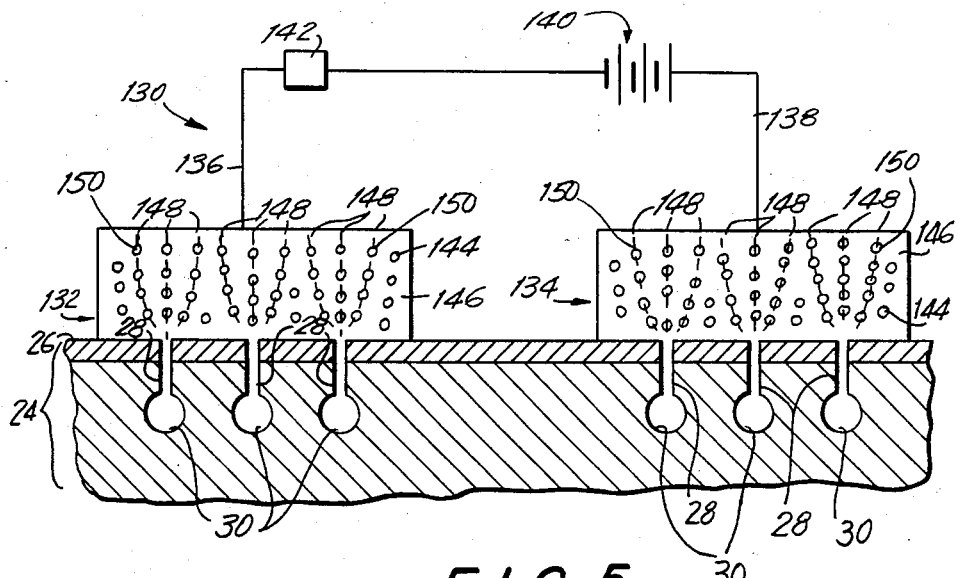
Figure 5A:
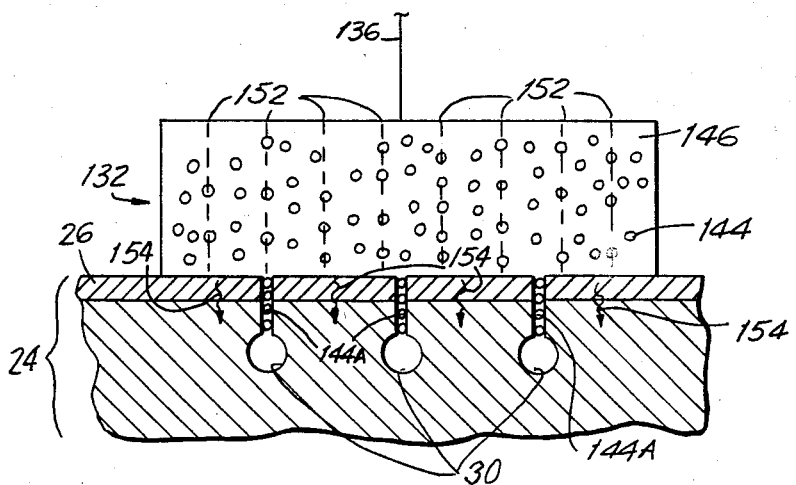
Figure 6:
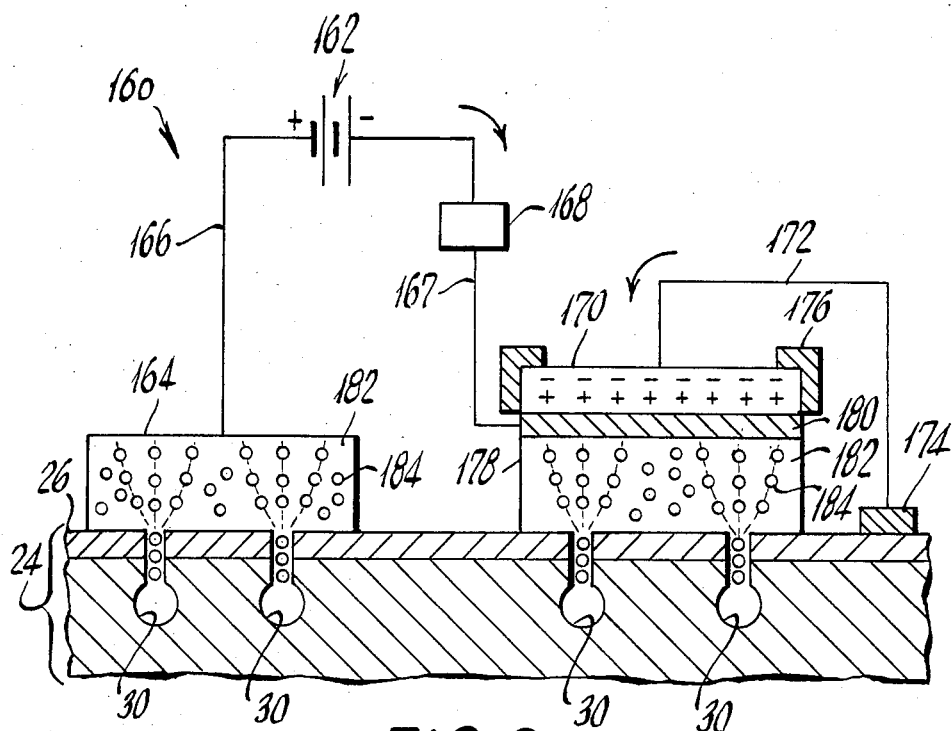

Yet another embodiment that reduces current level at the sweat glands is drug applicator system 130 shown in FIG. 5, which includes at least one drug reservoir or a plurality of drug reservoirs, shown here as two drug reservoirs 132 and 134 and electrical conductors 136 and 138 connected to opposite terminals of a battery 140 and to reservoirs 132 and 134, respectively. A current conditioner 142 is connected in series to one of the conductors, shown as conductor 136. Reservoirs 132 and 134 each contain a colloidal solution that comprises oil-based particles 144 and a water-based drug fluid medium 146. Medium 146 may also be described as being a solution of a water-soluble drug in water. Oil-based particles 144 can be large, as compared to the size of a molecule, inert oil particles, such as silicon oil particles, that, when battery 140 creates electrostatic field lines 148 shown in FIG. 5 that converge at sweat ducts 28, move in pearl chains 150 along electrostatic field lines 148 in accordance with the principle of dielectrophoresis to and into sweat ducts 28 so as to create a non-uniform electrostatic field in mediums 146. The inert oil particles, indicated as oil particles 144A in sweat ducts 28, clog the ducts. At this point, the low electrical resistivity of sweat ducts 28 is altered to a high resistivity generally equal to or even higher than stratum corneum 30 so that new electrostatic field lines are asserted more or less evenly throughout the volume of reservoirs 132 and 134 so as to create quasi-uniform electrostatic fields in mediums 146 therein. The water-soluble drug migrates and/or is delivered through the entire stratum corneum 30 in accordance with the principles of electrophoresis and electro-osmosis as is shown schematically by migration and delivery arrows in FIG. 5A, which shows reservoir 132 in isolation but being representative of reservoir 134 as well. Migration and delivery is greatly aided by the enhancement of skin permeability by the substantially even distribution of electrical current through the stratum corneum. Ionization of water-based mediums 146 occurs so as to create added phenomena related to the delivery of the drug. These phenomena are not described at this time.

A DC/DC or DC/AC converter (not shown) may optionally be used in lieu of battery 140.

Active oil-based drug particles capable of constricting sweat ducts 28 may be used instead of inert oil-based particles 144.

In general, where applicable, the colloidal suspensions discussed above may include two types of large liquid particles, or even a solid-type particle or particles, one of which is of a higher permittivity and the other of a lower permittivity than the fluid medium in which they are suspended. The particles of higher permittivity will pass into the sweat ducts. This high-permittivity particle may be an inert material with the function of plugging up the sweat ducts so that the other low-permittivity particle, which is a drug particle, will be absorbed through the stratum corneum. The high-permittivity particle that passes to the ducts may also be an active drug that is capable of constricting the sweat ducts.

The drug reservoirs can incorporate certain buffers to maintain a pH and a conductivity of the suspension medium which directly controls the orientation and movement of colloidal particles in an electrostatic field. It is also known that dielectrophoresis is capable of creating pressure gradients; such electrodynamic effects may be employed synergistically in the present invention to enhance the rate of transdermal delivery of a drug or drugs.

It will also be appreciated that although the embodiments of the invention have been described with reference to schematic and diagnostic illustrations, the transdermal drug applications of the present invention may include drug reservoirs of varied configurations, such as side-by-side reservoirs or a centrally disposed drug reservoir/electrode surrounded by the opposite polarity drug reservoir/electrode (picture-frame type construction).

Another embodiment of the invention is shown as drug applicator system 160, which includes a battery 162 connected to a drug reservoir 164 by a conductor 166 connected to the positive terminal of battery 162. Applicator system 160 also includes a permanently polarized electret 170 connected on its negative side to an electrostatic field conductor 172 that in turn is connected to a skin electrode 174 in electrical contact with skin 24, and in particular with stratum corneum 26, of the patient. Electret 170 is protected from voltage loss by insulator 176. Another drug reservoir 178 is in electrical connection to both electret 170 and conductor 172 at a common electrode 180 that is positioned between electret 170 and reservoir 178. Conductor 167 connects battery 162 with common electrode 180. Both drug reservoirs 164 and 178 contain colloidal suspensions of the type previously described relative to applicator system 10 including an oily fluid mediums 182 and large water-baed drug particles 184 having different permittivities from mediums 182.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A transdermal applicator system for passing at least one drug for delivery to the systemic circulation system of a patient through the skin having a plurality of sweat ducts opening at the stratum corneum, comprising, in combination,
a drug reservoir containing a colloidal suspension having at least one drug for delivery to the body of the patient, said colloidal suspension comprising a fluid medium and generally large, as compared to the size of molecules, particles in said medium, said medium and said particles being of different permittivities, said reservoir being capable of being placed in electrical contact with the skin of the patient,
voltage means for imposing electrostatic field lines upon said medium so as to create a non-uniform electrostatic field in said medium when said drug reservoir is placed on the skin,
said particles migrating in accordance with the principle of dielectrophoresis so as to pass through the skin into the systemic circulation system.

2. The transdermal applicator system described in claim 1, wherein said particles are water-based drug particles and said fluid medium is an oily fluid medium.

3. The transdermal applicator system described in claim 2, wherein said reservoir includes a skin side capable of being placed in electrical contact with the skin of the patient and an opposed side, and said voltage means includes a permanently polarized electret having opposed poles, one pole being connected with said opposed side, said electret imposing said electrical field lines in said medium between said opposed side and said skin side, said electrostatic field lines converging at the sweat ducts at the stratum corneum so as to create a non-uniform electrostatic field in said medium, whereby said water-based drug particles are moved along the electrostatic field lines into the seat ducts from where said drug particles are absorbed into the body when said skin side of said reservoir is placed in contat with the skin of the patient.

4. The transdermal applicator system described in claim 3, wherein the other pole of said electret is connected with said skin via the stratum corneum side of said reservoir.

5. The transdermal applicator system described in claim 4, further including an electrode capable of being in electrical contact with the skin of the patient and an electrostatic field conductor connecting said other pole of said electret with said electrode.

6. The transdermal applicator system described in claim 5, further including insulation means for precluding short-circuiting of said electret.

7. The transdermal applicator system described in claim 6, wherein said electret has a high internal charge sufficient to impose said electrostatic field lines upon said medium.

8. The transdermal drug applicator system described in claim 3, wherein said drug reservoir is a plurality of drug reservoirs.

9. The transdermal drug reservoir system described in claim 2, wherein said reservoir includes a skin side capable of being placed in electrical contact with the skin of the patient and an opposed side, said voltage means includes a battery having terminals, and an electrode capable of being connected to the skin of the patient, one of said terminals of said battery being electrically connected to said opposed side and the other of said terminals being connected to said electrode, wherein an electrical circuit is created when the skin side of the reservoir and the electrode are placed in contact with the skin of the patient, said battery imposing said electrostatic field lines in said medium between said opposed side and said skin side, said electrostatic field lines converging at the sweat ducts at the stratum corneum so as to create a non-uniform electrostatic field in said medium, whereby the water-based drug particles are moved along the electrostatic field lines into the sweat ducts from where the drug particles are absorbed into the body when the skin side of the reservoir and the electrode are placed in contact with the skin of the patient.

10. The transdermal drug applicator system described in claim 9, wherein said battery is a DC/DC converter.

11. The transdermal drug applicator system described in claim 9, wherein said battery is a DC/AC converter.

12. The transdermal drug applicator system described in claim 9, wherein said electrode is a second drug reservoir containing said colloidal suspension wherein said particles of said second drug reservoir are water-based drug particles and said fluid medium of said second drug reservoir is an oily fluid medium.

13. The transdermal applicator system described in claim 12, wherein said drug reservoir and said second drug reservoir include a plurality of drug reservoirs.

14. The transdermal drug system described in claim 2, wherein said drug reservoir includes a skin side capable of being placed in electrical contact with the skin of the patient and an opposed side, and further including a second drug reservoir including a second skin side capable of being placed in electrical contact with the skin of the patient and a second opposed side, said second drug reservoir containing a solution having a second drug; said voltage means including a battery having terminals and a permanently polarized electret having poles, one of said terminal of said battery being connected to said second opposed side of said second reservoir; and an electrode connected to one of said poles of said electret and adapted to be connected to the skin, the other pole of said electret being connected to said opposed side of said drug reservoir; said electret imposing said electrostatic field lines in said medium of said drug reservoir between said opposed side and said skin side, said electrostatic field lines converging at the sweat ducts at the stratum corneum so as to create a non-uniform electrostatic field in said medium, whereby said water-based drug particles are moved along the electrostatic field lines into the sweat ducts from where said drug particles are absorbed into the body; and an electrical circuit is created between the battery and the drug reservoir and the second reservoir so that delivery of the second drug from the second reservoir is accomplished when the skin side of the drug reservoir and the skin side of said second reservoir are placed in contact with the skin of the patient.

15. The transdermal drug applicator system described in claim 14, wherein said one terminal is the negative terminal and said other terminal is the positive terminal wherein the current moves in the electrical circuit from said battery to said electrode to said drug reservoir and through the skin to the skin side of said second reservoir.

16. The transdermal drug applicator system described in claim 15, further including another electrode capable of being in electrical contact with the skin of the patient and an electrostatic field conductor connecting the other pole of said electret with said another electrode.

17. The transdermal drug applicator system described in claim 16, said electret having positive and negative sides, said positive side being connected to said electrode and said negative side being connected to said another electrode.

18. The transdermal applicator system described in claim 17, further including insulation means for precluding short-circuiting of said electret.

19. The transdermal drug application system described in claim 2, wherein said reservoir means includes a skin side capable of being placed in electrical contact with the skin of the patient and an opposed side, and further including a second drug reservoir including a second skin side capable of being placed in electrical contact with the skin and a second opposed side, said second drug reservoir containing a second colloidal suspension having at least one drug for delivery to the body of the patient, said second colloidal suspension comprising a second fluid medium and generally large, as compared to the size of molecules, second particles in said second medium, said second medium and said second particles being of different permittivities; said voltage means including a battery having terminals and a permanently polarized electret having poles, one of said terminals of said battery being connectd to said second opposed side of said second reservoir; and an electrode connected to one of said poles of said electret and capable of being connected to the skin; the other pole of said electret being connected to said opposed side of said drug reservoir; said electret imposing said electrostatic field lines in said medium of said drug reservoir between said opposed side and said skin side said electrostatic field lines converging at the sweat ducts at the stratum corneum so as to create a non-uniform electrostatic field in said medium; said battery imposing electrostatic field lines in said second medium of said second drug reservoir between said second opposed side and said second skin side, said electrostatic field lines converging at the sweat ducts at the stratum corneum so as to create a non-uniform electrostatic field in said second medium; whereby said particles and said second particles are moved along the electrostatic field lines into the sweat ducts from where said particles and said second particles are absorbed into the body; and an electrical circuit is created between the battery and the drug reservoir and the second drug reservoir so that delivery of the second drug from the second reservoir is accomplished when the skin side of the drug reservoir and the skin side of the second drug reservoir are placed in contact with the skin of the patient.

20. The transdermal drug applicator system described in claim 1, wherein said particles are oil-based drug particles and said medium is a water medium.

21. The transdermal drug applicator system described in claim 20, further including an electrode capable of being connected to the skin of the patient, and wherein said reservoir includes a skin side capable of being placed in electrical contact with the skin of the patient and an opposed side, and said voltage means includes a battery having terminals, one of said terminals being connected to said opposed side and the other of said terminals being connected to said electrode, wherein an electrical circuit is created when the skin side of the reservoir and the electrode are placed in contact with the skin of the patient, said battery imposing said electrostatic field lines in said medium between said opposed side and said skin side, said electrostatic field lines converging at the sweat ducts at the stratum corneum so as to create a non-uniform field in said medium, whereby the oil-basic drug particles are moved along the electrostatic field lines into the sweat ducts from where the drug particles are absorbed into the body when the skin side of the reservoir and the electrode are placed in contact with the skin of the patient until the electrical resistance at the sweat ducts approximates the electrical resistance at the stratum corneum at which time electrical current passes throughout the stratum corneum and a quasi-uniform field is created in the reservoir and drug delivery is accomplished through the stratum corneum until the drug in the sweat ducts is absorbed and a non-uniform field is established in the reservoir and drug delivery is again accomplished through the sweat ducts.

22. The transdermal drug applicator system described in claim 21, wherein said one terminal is the positive terminal and said other terminal is the negative terminal.

23. The transdermal drug applicator system described in claim 22, wherein said electrode is a second drug reservoir containing said colloidal suspension wherein said particles of said second drug reservoir are water-based drug particles and said fluid medium of said second drug reservoir is an oily fluid medium.

24. The transdermal drug applicator system described in claim 23, wherein said drug reservoir and said second drug reservoir include a plurality of drug reservoirs.

25. The transdermal drug applicator system described in claim 1, wherein said particles are oil-based particles and said medium is a water-based drug fluid medium.

26. The transdermal drug applicator system described in claim 25, wherein said reservoir includes a skin side capable of being placed in electrical contact with the skin of a patient and an opposed side said voltage means includes a battery having terminals, and an electrode capable of being connected to the skin of the patient, one of said terminals of said battery being electrically connected to said opposed side and the other of said terminals being connected to said electrode, wherein an electrical circuit is created when the skin side of the reservoir and the electrode are placed in contact with the skin of the patient, said battery imposing said electrostatic field lines in said medium between said opposed side and said skin side, said electrostatic field lines converging at the sweat ducts at the stratum corneum so as to create a non-uniform electrostatic field in said medium, whereby the water-based drug fluid medium migrates into the body when the skin side of the reservoir and the electrode are placed in contact with the skin of the patient.

27. The transdermal drug applicator system described in claim 26, wherein said battery is a DC/DC converter.

28. The transdermal applicator system described in claim 27, wherein said battery is a DC/AC converter.

29. The transdermal drug applicator system described in claim 26, wherein said electrode is a second drug reservoir containing said colloidal suspension wherein said particles of said second drug reservoir are oil-based particles and said fluid medium of said second drug reservoir is a water-based drug fluid medium.

* * * * *